United States Patent

Guillaumet et al.

[11] Patent Number: 5,130,311
[45] Date of Patent: Jul. 14, 1992

[54] OXAZOLOPYRIDINE COMPOUNDS, COMPOSITIONS AND USE

[75] Inventors: Gérald Guillaumet, Orleans; Christine Flouzat, Clermont Ferrand; Michelle Devissaguet, Neuilly sur Seine; Pierre Renard, Versailles; Daniel H. Caignard, Paris; Gérard Adam, le Mesnil le Roi, all of France

[73] Assignee: Adir et Compagnie, Courbevoie, France

[21] Appl. No.: 792,423

[22] Filed: Nov. 15, 1991

[30] Foreign Application Priority Data

Nov. 20, 1990 [FR] France ................... 90 14381

[51] Int. Cl.$^5$ ................ A61K 31/435; A61K 31/535; C07D 498/04
[52] U.S. Cl. .................... 514/234.2; 514/212; 514/253; 514/302; 540/597; 544/127; 544/362; 546/116
[58] Field of Search ............... 540/597; 544/127, 362; 546/116; 514/212, 234.2, 253, 302

[56] References Cited

U.S. PATENT DOCUMENTS 3,929,809 12/1975 Kristinsson et al. ............ 546/116

Primary Examiner—Robert W. Ramsuer
Attorney, Agent, or Firm—Gordon W. Hueschen

[57] ABSTRACT

The invention relates to the analgesic compounds of general formula (I):

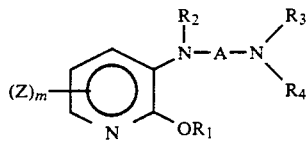

in which:
$R_1$, $R_2$, $R_3$, $R_4$, A, Z and m are as defined in the description, their isomers, epimers and diastereoisomers, their addition salts with a pharmaceutically acceptable acid and, when $R_1$ and $R_2$ each represent a hydrogen atom, their addition salts with a pharmaceutically acceptable base.

16 Claims, No Drawings

OXAZOLOPYRIDINE COMPOUNDS, COMPOSITIONS AND USE

The present invention relates to new oxazolo[5,4-b]pyridine compounds, to processes for preparing these and to pharmaceutical compositions containing them.

The properties, both analgesic and anti-inflammatory, of 2-phenyloxazolo[5,4- or -[5,4]pyridines are already known (Patents: U.S. Pat. Nos. 4,038,396, FR 2,328,471, FR 2,319,354, GB 1,421,619, U.S. Pat. No. 232, 740).

Howver, these compounds possess an essentially anti-inflammatory profile, as confirmed by the therapeutic indications metioned in the patents cited above, or else have the drawback of not dissociating the two types of activity: analgesic on the one hand, anti-pyretic and anti-inflammatory on the other hand.

The new compounds discovered by the Applicant posses not only a level of analgesic activity at least equivalent to that of the already known 2-phenyl-3H-oxazolo[4,5-b]- or -[5,4-b]pyridines, but also possess the very advantageous feature of being virtually devoid of anti-inflammatory effects.

Most non-morphinic analgesic substances known to data also possess anti-inflammatory activity and hence intervene in the processes linked to the phenomena of inflammation (this is the case, for example, with salicylate compounds such as aspirin, pyrazoles such as phenylbutazone, arylacetic or heteroarylacetic acids such as indomethacin, etc.). Being anti-inflammatory, these substances inhibit cyclooxygenase, thereby causing a blockade of the biosynthesis of numerous chemical mediators (prostaglandins, prostacycline, thromboxane A2, etc.). Multifarious side-effects hence ensue, including inhibition of platelet aggregation associated with disorders of coagulation, and a gastrointestinal toxicity with the possibility of ulcerations and of hemorrhage due to a decrease in the biosynthesis of prostaglandins PG $E_2$ and PG $F_1 \alpha$ which are cytoproptective of the gastric mucosa.

Apart from the problems they cause, these side-effects can, in many subjects who are espeically sensitive to them, make it impossible to prescribe substances endowed with anti-inflammatory properties.

Since the compounds of the present invention do not interact with the mediators of inflammation, they are hence devoid of the side-effects mentioned above.

This feature, combined with their absence of toxicity and their high level of activity, renders the compounds of the present invention usable as analgesics without the restrictions on their use which normally apply to the majority of the products of this class.

More specifically, the invention relates to the compounds of general formula (I):

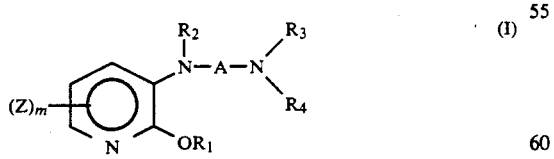

in which:

$R_1$ and $R_2$ each represent a hydrogen atom or, with the oxygen and the nitrogen which carry them, form an —O—CO—N—linkage, corresponding to oxazolo[5,4-b]pyridin-2-ones, Z represents halogen, linear or branched lower alkyl comprising from 1 to 6 carbon atoms, linear or branched lower alkoxy comprising from 1 to 6 carbona toms or trifluoromethyl, m is an integer which can take the values 0, 1, 2, 3, A is a linear or branched alkyl radical comprising from 1 to 6 carbon atoms, $R_3$ and $R_4$, which may be identical or different, represent:
hydrogen,
linear or branched lower alkyl comprising from 1 to 6 carbon atoms,
linear or branched lower alkenyl comprising from 1 to 6 carbona toms,
optionally substituted aryl or heteroaryl,
optionally substituted arylakyl or heteroarylalkyl in which the alkyl chain comprises from 1 to 3 carbon atoms,
mono- or bicyclic cycloalkyl having 3 to 10 carbon atoms, or alternatively:

$R_3$ and $R_4$, with the nitrogen atom to which they are linked, constitute a saturated or unsaturated, mono- or bicyclic, nitrogenous heterocyclic system comprising not more than 12 atoms, not counting the hydrogen atoms, which can include from one to three hetero atoms chosen from nitrogen, oxygen or sulfur, and optionally substituted with one or more:
hydroxyl,
oxo,
linear or branched lower alkyl comprising from 1 to 6 carbon atoms,
optionally substituted aryl,
optionally substituted arylalkyl or optionally substituted diarylalkyl in which the alkyl chain contains from 1 to 3 carbon atoms,

—CO—OR$_5$

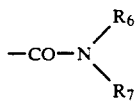

$R_5$ represents:
hydrogen,
linear or branched lower alkyl comprising from 1 to 6 carbon atoms,
optionally substituted aryl,
optionally substituted aralkyl in which the alkyl chain comprises from 1 to 3 carbon atoms, $R_6$ and $R_7$, which may be identical or different, have the same meaning as $R_5$, their isomers, epimers and diastereoisomers, their addition salts with a pharmaceutically acceptable acid and/or, when $R_1$ and $R_2$ each represent a hydrogen atom, their addition salts with a pharmaceutically acceptable base, aryl group being understood to mean an unsaturated or aromatic, mono- or bicyclic group comprising from 5 to 12 carbon atoms, heteroaryl group being understood to mean an unsaturated or aromatic, mono- or bicyclic group comprising from 5 to 12 atoms, not counting the hydrogen atoms, and incorporating in its carbon skeleton one, two or three hetero atoms chosen from nitrogen, oxygen or sulfur, the term substituted associated with the expressions aryl, arylalkyl, diarylalkyl, heteroacryl and heteroarylalkyl meaning that the aryl or heteroary ring-system or -systems can be substituted with one or more linear or branched lower alkyl group(s) having 1 to 6 carbon atoms, linear or branched lower alkoxy group(s) having 1 to 6 carbon atoms or hydroxyl, nitro, halogen or trifluoromethyl group(s).

The invention also encompasses the process for obtained the compounds of general formula (I), wherein a 3-amino-2-pyridinone of general formula (II):

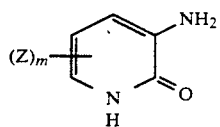
(II)

in which Z and m have the same meaning as in the compounds of general formula (I), is reacted in solution at $-78°$ C. (the temperature of an acetone/dry ice mixture) in an aprotic solvent or mixture of aprotic solvents with bis(trichloromethyl) carbonate (triphosgene) in the presence of a basic amine such as, for example, triethylamine so as to obtain a 1H-oxazolo[5,4-b]pyridine-2-one of general formula (III):

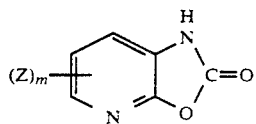
(III)

in which Z and m have the same meaning as in the compounds of general formula (I), which is reacted with an alkali metal alcoholate or hydride in an aprotic organic medium so as to obtain the compound of general formula (IV):

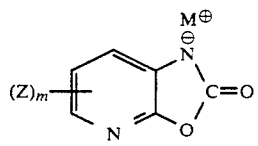
(IV)

in which Z and m have the same meaning as in the compounds of general formula (I) and M represents an alkali metal, which is reacted in an organic medium and at a temperature between room temperature and the refluxing temperature of the chosen solvent (or solvent mixture):

a) either with an electrophilic compound (preferably in excess) of general formula (V):

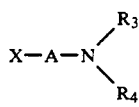
(V)

in which X represents a halogen atom and A, $R_3$ and $R_4$ have the same meaning as in the compounds of general formula (I), so as to obtain, after cooling, extraction and, where appropriate, purification, the compounds of general formula ($I_A$):

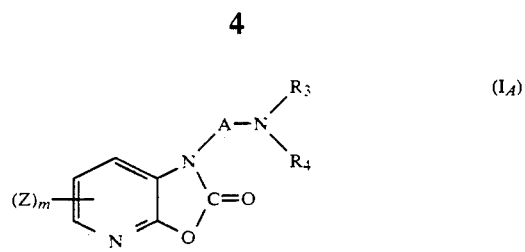
($I_A$)

a special case of the compounds of general formula (I) for which $R_1$ and $R_2$, with the oxygen and the nitrogen which carry them, form an

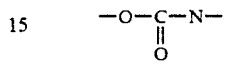

link, Z, m, A, $R_3$ and $R_4$ having the same meaning as in the compounds of general fromula (I), or with an electrophilic compound (preferably in excess) of general formula (VI):

X—A—X' (VI)

in which X and X', which may be identical or different, each represent a halogen atom, so as to obtain the halogenated compound of general formula (VII):

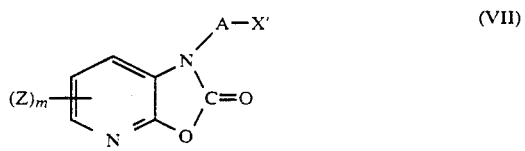
(VII)

in which X', A, Z and m have the same meaning as above, which is finally reacted with an amine (preferably in excess) of general formula (VIII):

(VIII)

in which $R_3$ and $R_4$ have the same meaning as in the compounds of formula (I), in an organic medium, optionally in the presence of a basic amine such as, for example, diisopropylamine and at a temperature between room temperature and the refluxing temperature of the chosen solvent, so as to obtain, after cooling, extraction and, where appropriate, purification, the compounds of general formula ($I_A$), c) or, in the special case of the compounds of general formula ($I_A$) in which A is a methylene link —$CH_2$—, with chloromethyl phenyl sulfide so as to obtain the compounds of general formula (IX):

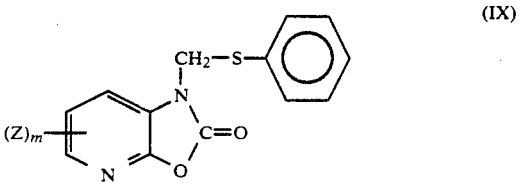
(IX)

in which Z and m have the same meaning as in the compounds of general formula (I), which is then reacted in an organic medium with sulfuryl chloride to obtain, after purification, the chlorinated compound of general formula (X):

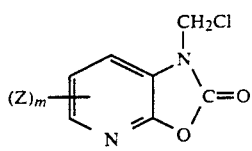

in which Z and m have the same meaning as in the compounds of general formula (I), which is then reacted as above with compounds of general formula (VIII) so as to obtain the compounds of general formula (I$_A$) with A being a methylene link —CH$_2$—.

The compounds of general formula (I$_A$) for which A is a methylene link —CH$_2$— may also be obtained in a single step by condensation in a lower aliphatic alcohol medium of the compound of general formula (III), an amine of general formula (VIII) in slight excess and an excess of formaldehyde at temeprature between room temperature and the refluxing temperature of the reaction medium, followed, after cooling and isolation, by an optional purification by chromatography on a silica column.

The compounds (I$_A$) obtained by the methods mentioned above can, if so desired, be separated into their isomers and/or salified with a pharmaceutically acceptable acid.

The compounds (I$_A$) can also, if so desired, be treated with an alkaline agent such as, for example, sodium hydroxide in aqueous solution at a temperature between room temperature and the refluxing temperature of the reaction medium to yield, after, where appropriate, acificication and/or neutralization of the reaction medium, the compounds of general formula (I$_B$):

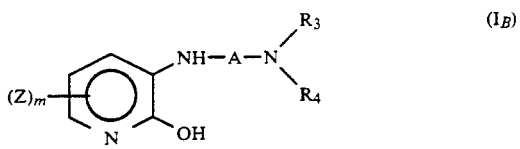

a special case of the compounds of general formula (I) of which $R_1=R_2=H$, and A, $R_3$, $R_4$, Z and m having the same meaning as in the compounds of general formula (I).

A pharmacological study of the compounds of the invention showed that they were of low toxicity, endowed with a high, pure analgesic activity and hence devoid of the drawbacks inherent in the anti-inflammatory component of non-morphinic compound exhibiting this type of activity (unlecerogenic action, interference with coagulation processes, etc.).

This pure analgesic activity renders the compounds of the present invention very advantageous in numerous indications such as rheumatic pain, lumbosciatic neuralgia, cervicobrachial neuralgia, pain associated with trauma such as sprains, fractures, dislocations, posttraumatic pain, postoperative pain, dental pain, neurological pain such as facial neuralgia, visceral pain such as nephritic colic, dysmenorrhea, proctological surgery, pain in the ENT region, pancreatitis, various pains, headache, cancer pain, etc.

The subject of the present invention is also pharmaceutical compositions containing the products of formula (I) or one of their addition salts with a pharmaceutically acceptable acid, alone or in combination with one or more pharmaceutically acceptable, non-toxic, inert excipients or vehicles.

Among the pharmaceutical compositions according to the invention, there may be mentioned, more especially, those which are suitable for oral, parenteral, nasal, rectal, perlingual, occular or respiratory administration, and in particular injections, aerosols, eye or nasal drops, simple or sugar-coated tablets, sublingual tablets, sachets, packets, hard gelating capsules, sublingual preparations, troches, suppositories, creams, ointments, skin gels, and the like.

The appropriate dosage varies according to the patient's age and weight, the administration route and the nature of the therapeutic indication and of any associated treatment, and lies between 10 mg and 4 grams per 24 hours.

The examples which follow illustrate the invention and in no way limit it.

EXAMPLE 1:
1-[2-(4-PHENYL-1-PIPERAZINYL)ETHYL]-1H-OXAZOLO[5,4-b]PYRIDIN-2-one

Stage A: 1H-Oxazolo[5,4-b]Pyridine-2-One

A solution of 0.33 g (3 mmol) of 3-amino-2-hydroxypyridine in a 50:50 mixture of dichloromethane and anhydrous tetrahydrofuran is cooled to $-78°$ C. (the temperature of an acetone/dry ice mixture) under an inert atmosphere (argon). 2.2 cm$^3$ (15 mmol) of triethylamine are added, and 0.98 g (3.3 mmol) of bis(trichloromethyl) carbonate (triphosgene) dissolved in 10 cm$^3$ of a 50:50 mixture of dichloromethane and tetrahydrofuran is then run in dropwise.

After 30 minutes' stirring, a further 2.2 cm$^3$ (15 mmol) of triethylamine are added and stirring is maintaed for six hours.

After evaporation of the solvent under reduced pressure, the crystals obtained are purified by flash chromatography on a silica column (eluent: ethyl ether/tetrahydrofuran, 50:50).

1H-Oxazolo[5,4-b]pyridin-2-one is finally obtained in a 78% yield.

Melting point: 252° C.

IR (KBr disk) 3220 cm$^{-1}$ (weak) $\nu$NH, s 2900-3000 cm$^{-1}$ $\nu$CH, s 1775 cm$^{-1}$ $\nu$C=0.

$^1$H NMR (CDCl$_3$, TMS): δ: 11.8 ppm, 1H, singlet NH δ: 7.92 ppm, 1H, doublet of doublet (J=5 Hz and J=1.5 Hz) H (5), δ: 7.46 ppm, 1H, doublet of doublet (J=8 Hz and J=1.5 Hz) H (7), δ: 7.17 ppm, 1H, doublet of doublet (J=8 Hz and J=5 Hz) H (6).

METHOD A

Stage B:
1-(2-Bromoethyl)-1H-Oxazolo[5,4-b]Pyridin-2-one 1.36 g (10 mmol) of 1H-oxazolo[5,4-b]pyrindin-2-one are dissolved in 80 cm$^3$ of dimethylformamide under an inert atmosphere (argon). 15 mmol of sodium hydride, washed beforehand with tetrahydrofuran, are then added at room temperature and in small portions.

The mixture is heated to 50° C. for 40 minutes and then cooled to room temperature, and 5.17 cm$^3$ (60 mmol) of dibromoethane diluted in 20 cm$^3$ of dimethylformamdide are added.

The mixture is heated to 110° C. for one hour and the dimethylformamide is then removed by distillation under reduced pressure.

The residue is taken up with water, the aqueous phase is extracted with methylene chloride, the organic phases are dried over magnesium sulfate and then taken to dryness and the crude porduct is purified by flash chromatography on a silica column (230-240 mesh silica; eluent: acetonitrile/methylene chloride, 5:95).

1-(2-Bromoethyl)-1H-oxazolo[5,4-b]pyridin-2-one is finally obtained in a 66% yield.

Melting point: 109°-110° C.

IR (KBr disk): 2900-300 cm$^{-1}$ $\nu$CH, 1760 cm$^{-1}$ $\nu$C=0.

$^1$H NMR (CDCl$_3$, TMS): δ: 8.7 ppm, 1H, doublet of doublet (J=5.1 Hz and J=1.5 Hz) H (5), δ: 7.37 ppm, 1H, doublet of doublet (J=7.7 Hz and J=1.5 Hz) H (7), δ: 7.17 ppm, 1H, doublet of doublet (J=5.1 Hz and J=7.7 Hz) H (6), δ: 4.27 ppm, 2H, triplet (J=6.3 Hz) CH$_2$—N, δ: 3.7 ppm, 2H, triplet (J=6.3 Hz) CH$_2$.

Stage C:
1-[2-(4-Phenyl-1-Piperazinyl)Ethyl]-1H-Oxazolo[5,4-b]Pyridin-2-One

In a round-bottomed flask under an argon atmosphere, surmounted by a condenser, 2.43 g (15 mmol) of 1-phenylpiperazine and then 2.61 cm$^3$ (15 mmol) of diiso-propylethylamine are added to a solution of 2.43 g (10 mmol) of 1-(2-bromoethyl)-1H-oxazolo [5,4-b]pyridin-2-one in acetonitrile.

The mixture is brought to 80° C. for 12 hours and then allowed to cool, and the acetonitrile is evaporated off under reduced pressure.

The residue is taken up in water, the alkalinity of the medium is checked, the aqueous phase is extracted with methylene chloride and the methylene chloride phases are dried over magnesium sulfate and taken to dryness.

The crude product obtained is then purified by chromatography on a silica column (230-240 mesh silica; eluent: methylene chlroide/methanol, 95:5).

1-[2-(4-Phenyl-1-piperazinyl)ethyl]-1H-oxazol-[5,4-b]pyridin-2-one is finally obtained in a 90% yield.

Melting poihnt: 182°-183° C.

IR (KBr disk) 2900-3100 cm$^{-1}$ $\nu$C=0.

$^1$H NMR (CDCl$_3$, TMS): δ: 8.03 ppm, 1H, doublet of doublet (J=5 Hz and J=1.3 Hz) H (5), δ: 7.3 ppm, 1H, doublet of doublet (J=7.6 Hz and J=1.3 Hz) H (7), δ: 7.25 ppm, 2H, doublet, aromatic H, δ: 7.13 ppm, 1H, doublet of doublet (J=5 Hz and J=7.6 Hz) H (6), δ: 4 ppm, 2H, triplet (J=6 Hz) CH$_2$—N, δ: 3.15 ppm, 4H, multiplet, piperazine H, δ: 2.77 ppm, 2H, triplet (J=6 Hz) CH$_2$, δ: 2.68 ppm, 4H, multiplet, piperazine H.

METHOD B

Stage B: 4-Phenyl-1-(2-Chloroethyl)Piperazine 6.49 g (40 mmol) of 1-phenylpiperazine are dissolved under argon in 40 cm$^3$ of diemthylformamide, and 6.63 g (48 mmol) of anhydrous potassium carbonate and then 6.88 g (48 mmol) of 1-bromo-2-chloroethane are added.

The mixture is stirred at room temperature for 22 hours and the insoluble inorganic matter is then removed by filtration.

The filtrate is acidified with ethanol saturated with dry phydrochloric acid to Ph 1.

400 cm$^3$ of anhydrous ethyl ester are added the 4-phenyl-1-(2-chloroethyl)piperazine, which precipitates in the medium, is isolated by taking to dryness.

The hydrochloride is taken up in 10% aqueous sodium carbonate solution and the aqueous phase is then extracted with methylene chloride.

The organic phase is dried over magnesium sulfate, filtered and then taken to dryness under reduced pressure.

The 4-phenyl-1-(2-chloroethyl)piperazine obtained is employed in the next step without further treatment.

Stare C:
1-[2-(4-Phenyl-1-Piperazinyl)Ethyl]-1H-Oxazolo[5,4-b]Pyridin-2-One 15 mmol of sodium hydride, washed beforehand with THF, are added in small portins to a solution, under an argon atmosphere, of 1.36 g (10 mmol) of 1-oxazolo[5,4-b]pyridin-2-one in 80 cm$^3$ of dimethylformamide.

The mixture is heated to 50° C. for 40 minutes and then cooled, and 12 mmol of 4-phenyl-1-(2-chloroethyl)-piperazine dissolved in 20 cm$^3$ of dimethylformamide are added at room temperature.

The mixture is brought to reflux ($\simeq$153° C.) for 90 minutes. The residue is taken up with water, the aqueous phase is extracted with methylene chloride and the methylene chloride phases are dried over magnesium sulfate and taken to dryness.

The crude product obained is then purified on a silica column (230-240 mesh silica; eluent: methylene chloride/methanol, 95:5).

1-[2-(4-Phenyl-1-piperazinyl)ethyl]-1H-oxazolo-[5,4-b]pyridin-2-one is obtained in a 64% yield.

EXAMPLE 2:
1-{2-[4-(3-TRIFLUOROMETHYLPHENYL)-1-PIPERAZINYL]ETHYL}-1H-OXAZOLO[5,4-b]PYRIDIN-2-ONE

Both methods of synthesis described in Example 1 may be used, replacing 1-phenylpiperazine by 1-(3-trifluoromethylphenyl)piperazine.

Melting point: 99°-100° C.

IR (KBr disk) 2700-3000 cm$^{-1}$ $\nu$CH, 1765 cm$^{-1}$$\nu$C=0.

$^1$H NMR (CDCl$_3$, TMS): δ: 8.03 ppm, 1H, doublet of doublet (J=5.4 Hz and J=1.3 Hz) H(5), δ: 7.3 ppm, 3H, multiplet H (7)+aromatic 2H, δ: 7.14 ppm, 1H, doublet of doublet (J=7.3 Hz and J=5.4 Hz) H(6), δ: 7.14 ppm, 1H, doublet of doublet (J=7.3 Hz and J=5.4 Hz) H(6), δ: 7.0-7.08 ppm, 2H, multiplet, aromatic 2H, δ: 3.98 ppm, 2H, triplet (J=6.3 Hz) N—CH$_2$, δ: 3.16 ppm, 4H, multiplet, piperazine 2 CH$_2$, δ: 2.78 ppm, 2H, tripolet (J=6.3 Hz) CH$_2$, δ: 2.67 ppm, 4H, multiplet, piperazine 2 CH$_2$.

EXAMPLE 3:
1-(2-MORPHOLINOETHYL)-1H-OXAZOLO-[5,4-b]PYRIDIN-2-ONE

Both methods of synthesis described in Example 1 may be used, replacing 1-phenylpiperazine by morpholine.

Melting point: 102°-103° C.

IR (KBr disk) 2700-3000 cm$^{-1}$ $\nu$CH.

$^1$H NMR (CDCl$_3$, TMS): δ: 8.06 ppm, 1H, doublet of doublet (J=5 Hz and J=1.4 Hz) H(5), δ: 7.27 ppm, 1H, doublet of doublet (J=7.9 Hz and J=1.4 Hz) H(7), δ: 7.14 ppm, 1H, doublet of doublet (J=7.9 Hz and J=5 Hz) H (6), δ: 3.93 ppm, 2H, triplet (J=6.2 Hz) CH$_2$, δ: 3.63 ppm, 4H, multiplet, morpholine 2 CH$_2$, δ: 2.49 ppm, multiplet, morpholine CH$_2$,

EXAMPLE 4:
1-{2-[4-(4-FLUOROPHENYL)-1-PIPERAZINYL]ETHYL}-1H-OXAZOLO[5,4-b]PYRIDIN-2-ONE

Both methods of synthesis described in Example 1 may be used, replacing 1-phenylpiperazine by 1-(4-fluoro-phenyl)piperazine.

Melting point: 135° C.

IR (KBr disk) 3100–2800 cm$^{-1}$ $\nu$CH, 1760 cm$^{-1}$ $\nu$C=0.

$^1$H NMR (CDCl$_3$, TMS): $\delta$: 8,04 ppm, 1H, doublet of doublet (J=5,1 Hz and J=1,6 Hz) H (5), $\delta$: 7,3 ppm, 1H, doublet of doublet (J=7,5 Hz and J=1,6 Hz) H (7), $\delta$: 7,14 ppm, 'H, doublet of doublet (J=7,5 Hz and J=5,1 Hz) H (6), $\delta$: 6,8–6,99 ppm, 4H, multiplet, aromatic H, $\delta$: 3,98 ppm, 2H, triplet (J=6,1 Hz) CH$_2$, $\delta$: 3,03–3,08 ppm, 4H, multiplet, piperazine CH$_2$, $\delta$: 2,78 ppm, 2H, triplet, (J=6,1 Hz) CH$_2$, $\delta$: 2,66–2,72 ppm, 4H, multiplet, piperazine CH$_2$.

EXAMPLE 5:
1-{2-[4-(2-Methoxyphenyl)-1-PIPERAZINYL]ETHYL}-1H-OXAZOLO[5,4-b]PYRIDIN-2-ONE Both methods of synthesis described in Example 1 may be used, replacing 1-phenylpiperazine by 1-(2-methoxyphenyl)piperazine.

Melting point: 146° C.

IR (KBr disk) 3100–2725 cm$^{-1}$ $\nu$CH, 1770 cm$^{-1}$ $\nu$C=0.

$^1$H NMR (CDCl$_3$, TMS): $\delta$: 8,03 ppm, 1H, doublet of doublet (J=5,1 Hz and J=1,2 Hz) H (5), $\delta$: 7,32 ppm, 1H, doublet of doublet J=7,5 Hz and J=1,2 Hz) H (7), $\delta$: 7,14 ppm, 1H, doublet of doublet (J=7,5 Hz and J=5,3 Hz) H (6), $\delta$: 6,84–7,03 ppm, 5H, multiplet, aromatic H, ": 3,99 ppn, 2H, triplet (J=6,3 Hz) CH$_2$, $\delta$3,86 ppm, 3H, singlet OCH$_3$, $\delta$: 2,99–3,08 ppm, 4H, multiplet, piperazine CH$_2$, $\delta$: 2,79 ppm, 2H, triplet, (J=6,3 Hz) CH$_2$, $\delta$: 2,69–2,75 ppm, 4H, multiplet, piperazine CH$_2$.

EXAMPLE 6:
1-{2-(4-PHENYL-1-PIPERIDYL)ETHYL}-1H-OXAZOLO[5,4-b]PYRIDIN-2-ONE

Both methods of synthesis described in Example 1 may be used, replacing 1-phenylpiperazine by 4-phenyl-piperidine.

Melting point: 128° C.

IR (KBr disk) 3100–2725 cm$^{-1}$ $\nu$CH, 1760 cm$^{-1}$ $\nu$C=0.

$^1$H NMR (CDCl$_3$, TMS): $\delta$: 8,04 ppm, 1H, doublet of doublet (J=5,1 Hz and J=1,6 Hz) H (5), $\delta$: 7,10–7,34 ppm, 7H, multiplet H (6), H(7) and 5 aromatic H, $\delta$: 3,98 ppm, 2H, triplet (J=6,3 Hz) CH$_2$, $\delta$: 3,01–3,08 ppm, 2 H, multiplet, piperidine CH$_2$, $\delta$: 2,75 ppm, 2H, triplet, (J=6,3 Hz) CH$_2$, $\delta$: 2,44–2,55 ppm, 1H, multiplet, piperidine CH$_2$, $\delta$: 2,13–2,26 ppm, 2H, multiplet, piperidine CH$_2$, $\delta$: 1,60–1,88 ppm, 4H, multiplet piperrdine CH$_2$.

EXAMPLE 7:
1-[2-(1-PYRROLIDINYL)ETHYL}-1H-OXAZOLO≡5,4-b]PYRIDIN-2-ONE

Both methods of synthesis described in Example 1 may be used, replacing 1-phenylpiperazine by pyrrolidine.

Melting point: 99°–91° C.

IR (KBr disk) 3080–2700 cm$^{-1}$ $\nu$CH, 1750 cm$^{-1}$ $\nu$C=0.

$^1$H NMR (CDCl$_3$, TMS): $\delta$: 8,02 ppm, 1H, doublet of doublet (J=5,1 Hz and J=1,4 Hz) H (5), $\delta$: 7,29 ppm, 1H, doublet of doublet (J=7,5 Hz and J=1,4 Hz) H (7), $\delta$: 7,12 ppm, 1H, doublet of doublet (J=7,5 Hz and J=5,1 Hz) H(6), $\delta$: 3,96 ppm, 2H, triplet (J=6,3 Hz) CH$_2$, $\delta$: 2,84 ppm, 2H, triplet, (J=6,3 Hz) CH$_2$, $\delta$: 2,54–62 ppm, 4H, multiplet, pyrrolidine CH$_2$, $\delta$: 1,73–1,81 ppm, 4H, multiplet, pyrrolidine CH$_2$.

EXAMPLE 8:
1-[2-(HEXAMETHYLENIMINO)ETHYL]-1H-OXAZOLO[5,4-b]PYRIDIN-2-ONE

Both methods of synthesis described in Example 1 may be used, replacing 1-phenylpiperazine by hexamethylenimine.

Melting point: 86° C.

IR (KBr disk) 3080–2700 cm$^{-1}$ $\nu$CH, 1750 cm$^{-1}$ $\nu$C=0.

$^1$H NMR (CDCl$_3$, TMS): $\delta$: 8,02 ppm, 1H, doublet of doublet (J=5,2 Hz and J=1,3 Hz) H (5), $\delta$: 7,13 ppm, 1H, doublet of doublet (J=7,8 Hz and J=1,3 Hz) H(7), $\delta$: 7,14 ppm, 1H, doublet of doublet (J=7,8 Hz and J=5,2 Hz) H (6), $\delta$: 3,89 ppm, 2H, triplet (J=6,5 Hz) CH$_2$, $\delta$: 2,87 ppm, 2H, triplet, (J=6,5 Hz) CH$_2$, $\delta$: 2,64–2,72 ppm, 4H, multiplet CH$_2$, $\delta$: 1,50–1,65 ppm, 1H, multiplet CH$_2$.

EXAMPLE 9:
1-(3-MORPHOLINO-1-PROPYL)-1H-OXAZOLO-[5,4-b]PYRIDIN-2-ONE

Stage A:
1-(3-Bromopropyl)-1H-OXAZOLO[5,4-b]-Pyridin-2-One

The procedure is as for 1-(2-bromoethyl)-1H-oxazolo[5,4-b]pyridin-2-one (Example 1, Method A, stage B), replacing 1,2-dibromoethane by 1,3-dibromopropane.

1-(3-Bromopropyl)-1H-oxazolo[5,4-b]pyridin-2-one is obtained in a 57% yield.

Melting point: 62°–63° C.

IR (KBr disk) 2900–3100 cm$^{-1}$ $\nu$CH, 1760 cm$^{-1}$ $\nu$C=0.

$^1$H NMR (CDCl$_3$, TMS): $\delta$: 8 ppm, 1H, doublet of doublet (J=5.2 Hz and J=1.4 Hz) H (5), $\delta$: 7.38 ppm, 1H, doublet of doublet (J=8 Hz and J=1.4 Hz) H (7), $\delta$: 7.17 ppm, 1H, doublet of doublet (J=5.2 Hz and J=8 Hz) H (6), $\delta$: 4 ppm, 2H, triplet (J=6.3 Hz) CH$_2$N, $\delta$: 3.45 ppm, 2H, triplet (J=6.3 Hz) CH$_2$, $\delta$: 2.37 ppm, 2H, multiplet CH$_2$.

Stage B:
1-(3-Morpholino-1-Propyl)-1H-Oxazolo-[5,4-b]Pyridin-2-One

The procedure is as for 1-[2-(4-phenyl-1-piperazinyl)ethyl]-1H-oxazolo[5,4-b]pyridin-2-one (Example 1, Method A, stage C), replacing 1-(2-bromoethyl)-1H-oxazolo[5,4-b]pyridin-2-one by 1-(3-bromopyropyl)-1-H-oxazolo[5,4-b]pyridin-2-one and 1-phenylpiperazine by morpholine.

Yield: 72%

Melting point: 170°–171° C.

IR (KBr disk) 2700–3100 cm$^{-1}$ $\nu$CH, 1760 cm$^{-1}$ $\nu$C=0.

$^1$H NMR (CDCl$_3$, TMS): $\delta$: 8.04 ppm, 1H, doublet of doublet (J=5.2 Hz and J=1.5 Hz) H(5), $\delta$: 7.32 ppm, 1H, doublet of doublet (J=7.4 Hz and J=1.5 Hz) H(7) $\delta$: 7.14 ppm, 1H, doublet of doublet (J=7.4 Hz and J=5.2 Hz) H(6) δ: 3.95 ppm, 2H, triple (J=6.6 Hz) CH₂, δ: 3.26 ppm, 2H, multiplet, morpholine 2 CH₂, δ: 2.4 ppm, 2H, triplet (J=6.6 Hz) CH₂, δ: 2.35 ppm, 4H, multiplet, morpholine 2 CH₂, δ: 1.96 ppm, 2H, multiplet CH₂.

EXAMPLE 10:
1-[3-(4-PHENYL-1-PIPERAZINYL)-1-PROPYL]-1H-OXAZOLO[5,4-b]PYRIDIN-2-ONE

The procedure is as for 1-(3-morpholinopropyl)-1H-oxazolo[5,4-b]pyridin-2-one, replacing morpholine in stage B by 1-phenylpiperazine.

Melting point: 119° C.

IR (KBr disk) 3100-2760 cm⁻¹ νCH, 1760 cm⁻¹ νC=0.

¹H NMR (CDCl₃, TMS): δ: 8,02 ppm, 1H, doublet of doublet (J=5,1 Hz and J=1,6 Hz) H(5), δ: 7,26 ppm, 2(J=7,9 Hz) aromatic H, δ: 7,12 ppm, 1H, doublet of doublet (J=7,9 Hz and J=5,1 Hz) H (6), δ: 6,91 ppm, 2H, doublet (J=7,9 Hz) aromatic H, δ: 6,85 ppm, 1H, triplet (J=7,9 Hz) aromatic H, δ: 3,96 ppm, 2H, triplet (J=6,7 Hz) CH₂, δ: 3,09-3,16 ppm, 4H, multiplet piperazine CH₂, δ: 2,5-2,55 ppm, 4H, multiplet piperazine CH₂, δ: 2,45 ppm, 2H, triplet (J=6,7 Hz) CH₂, δ: 2,00 ppm, 2H, quadruplet (J=6,7 Hz) CH₂.

EXAMPLE 11:
1-(4-MORPHOLINO-1-n-BUTYL)-1H-OXAZOLO[5,4-b]PYRIDIN-2-ONE

Stage A:
1-(4-Bromobutyl)-1H-Oxazolo[5,4-b]-Pyridin-2-One

The procedure is as for 1-(2-bromoethyl)-1H-oxazolo[5,4-b]pyridin-2-one (Example 1, Method A, stage B), replacing 1,2-dibromoethane by 1,4-dibromobutane.

Yield: 62%
Melting point: 60°-61° C.

IR (KBr disk) 2900-3100 cm⁻¹ νCH, 1760 cm⁻¹ νC=0.

¹H NMR (CDCl₃, TMS): δ: 8.05 ppm, 1H, doublet of doublet (J=5.1 Hz and J=1.5 Hz) H(5), δ: 7.28 ppm, 1H, doublet of doublet (J=7.9 Hz and J=1.5 Hz) H(7), δ: 7.16 ppm, 1H, doublet of doublet (J=7.9 Hz and J=5.1 Hz) H(6), δ: 3.913 ppm, 2H, triplet (J=6.5 Hz) CH₂, δ: 3.46 ppm, 2H, triplet (J=5.9 Hz) CH₂.

Stage B:
1-(4-Morpholino-1-n-Butyl)-1H-Oxazolo-[5,4-b]Pyridin-2-one

The procedure is as for 1-[2-(4-phenyl-1-piperazinyl)ethyl]-1H-oxazolo[5,4-b]pyridin-2-one (Example 1, Method A, stage C), replacing 1-(2-bromoethyl)-1H-oxazolo[5,4-b]pyridin-2-one by 1-(4-bromobutyl)-1H-oxazolo[5,4-b]pyridin-2-one and 1-phenylpiperazine by morpholine.

Yield: 76%
Melting point: 108°-109° C.

IR (KBr disk) 2700-3000 cm⁻¹√CH, 1760 cm⁻¹√C=0.

¹H NMR (CDCl₃, TMS): δ: 8.02 ppm, 1H, doublet of doublet (J=5.2 Hz and J=1.5 Hz) H(5), δ: 7.25 ppm, 1H, doublet of doublet (J=7.4 Hz and J=1.5 Hz) H(7), δ: 7.14 ppm, 1H, doublet of doublet (J=7.4 Hz and J=2.5 Hz) H(6), δ: 3.88 ppm, 2H, triplet (J=7.1 Hz) CH₂, δ: 3.7 ppm, 2H, multiplet, morpholine 2H, δ: 43-2.46 ppm, 4H, multiplet, morpholine CH₂+2H, δ: 1.48 ppm, 2H, multiplet, morpholine 2H.

EXAMPLE 12:
1-[4-(4-PHENYL-1-PIPERAZINYL)-1-n-BUTYL]-1H-OXAZOLO[5,4-b]PYRIDIN-2-ONE

The procedure is as for 1-(4-morpholino-1-n-butyl)-1H-oxazolo[5,4-b]pyrindin-2-one, replacing morpholine in stage B by 1-phenylpiperazine.

Melting point: 94° C.

IR (KBr disk) 2960-2760 cm⁻¹√CH, 1765 cm⁻¹√C=0.

¹H NMR (CDCl₃, TMS): δ: 8,03 ppm, 1H, doublet of doublet (J=5,1 Hz and J=1,4 Hz) H (5), δ: 7,21 ppm, 3H, multiplet H (7) and aromatic 2H, δ: 7,15 ppm, 1H, doublet of doublet (J=7,9 Hz and J=5,1 Hz) H (6), δ: 6,92 ppm, 2H, doublet (J=7,5 Hz) aromatic H, δ: 6,84 ppm, 1H, triplet (J=7,5 Hz) aromatic H, δ: 3,88 ppm, 2H, triplet (J=7,5 Hz) CH₂, δ: 3,16-3,22 ppm, 4H, multiplet piperazine CH₂, δ: 2,54-2,61 ppm, 4H, multiplet piperazine CH₂, δ: 2,46 ppm, 2H, triplet (J=7,5 Hz) CH₂, δ: 1,80-1,92 ppm, 2H, multiplet CH₂,

EXAMPLE 13:
1-{2-[4(N,N-DIETHYLAMINOCARBONYL)-1-PIPERAZINYL]ETHYL}-1H-OXAZOLO[5,4-b]PYRIDIN-2-ONE

Both methods of synthesis described in Example 1may be used, replacing 1-phenylpiperazine by 1-(N,N-diethyl aminocarbonyl) piperazine Melting point: 137° C.

IR (KBr disk) 3100-2800 cm⁻¹ νCH, 1765 cm⁻¹ νC=0.

¹H NMR (CDCl₃, TMS): δ: 8,02 ppm, 1H, doublet of doublet (J=5,2 Hz and J=1,3 Hz) H (5), δ: 7,27 ppm, 1H, doublet of doublet (J=7,8 Hz and J=1,3 Hz) H (7), δ: 7,12 ppm, 1H, doublet of doublet (J=7,8 Hz and J=5,2 Hz) H (6), δ: 3,94 ppm, 2H, triplet (J=2,3 Hz) CH₂, δ: 3,12 and 3,33 ppm, 8H, multiplet CH₂, δ: 2,71 ppm, 2H, triplet (J=2,3 Hz) CH₂, δ: 2,5 ppm, 4H, triplet (J=1,7 Hz) piperazine CH₂, δ: 1,10 ppm, 6H, triplet (J=5,3 Hz) CH₃.

EXAMPLE 14:
3-[2-(4-PHENYL-1-PIPERAZINYL)ETHYL-AMINO]-2-HYDROXYPYRIDINE

A solution of 1 mol of 1-[2-(4-phenyl-1-piperazinyl)ethyl]-1H-oxazolo-[5,4-b]pyridin-2-one (obtained in Example 1) in 50 cm³ of 10% aqueoius sodium hydroxide solution is heated to reflux for 4 hours.

After cooling, the aqueous solution is slightly acidified by adding 30% aqueous hydrochloric acid and then neutralized to pH 7 with saturated aqueous sodium bicarbnate solution.

The precipitate obtained is filtered off, washed three times with water and then dried.

PHARMACOLOGICAL STUDY OF THE COMPOUNDS OF THE INVENTION

A. TESTING FOR ANALGESIC ACTIVITY

1) Acetic acid-induced cramps: "Acetic acid writhing"

The analgesic poential of these compounds was investigated according to the so-called "acetic acid writhing" test (or alternatively "KOSTER" test), which is based on counting the abdominal cramps induced in rats by the intraperitoneal injection of acetic acid.

Male Wistar rats randomized in batches of 5 (weight 150±10 g) received the test compounds orally 30 min before the intraperitoneal injection of 1 cm³ of 1% acetic acid.

The number of cramps is counted during the 25 minutes following the injection.

The percentage activity was assessed for each compound (% decrease in the number of cramps in the treated animals relative to the controls).

2) Phenylbenzoquinone-induced cramps: "PBQ writhing"

The analgesic potential of these compounds was investigated according to the so-called "PBQ wrigthing" test (or alternatively "SIGMUND" test), which is based on counting the cramps induced in mice by the intraperitoneal injection of phenylbenzoquinone.

Male CD-1 mice randomized in batches of 5 received the test compounds orally 30 min before the intraperitoneal injection of 0.25 cm³ of a 0.01% solution of phenylbenzoquinone in a 95:5 water/ethanol mixture.

The number of cramps is counted between the 5th and the 15th minute after the injection of phenylbenzoquinone.

The percentage activity was assessed for each compound (% decrease in the number of cramps in the treated animals relative to the controls).

3) Results

| PRODUCT | DOSE | Acetic Acid Whrithing % inhibition | PBQ Whrithing % inhibition |
|---|---|---|---|
| Aspirin | 50 mg/kg | 69% | 70% |
| 1-[3-(4-phenyl piperazinyl)-1-propyl]-1H-oxazol [5,4-b] pyridin-2-one | 50 mg/kg | 92% | 98% |
| 1-[4-(4-phenyl-1-piperazinyl)-1-butyl]-1H-oxazolo [5,4-b] pyridin-2-one | 50 mg/kg | 96% | 91% |
| 1-[2-(4-(4-fluoro-phenyl)-1-piperazinyl) ethyl]-1H-oxazolo - [5,4-b] pyridin-2-one | 50 mg/kg | 84% | 83% |

It is apparent that the compounds of the invention possess a very advantageous analgesic activity, which is very significantly greater than that of aspirin.

B. TESTING FOR ANTI-INFLAMMATORY ACTIVITY

The anti-inflammatory potential of the compounds was investigated on a model of acute inflammation caused by the subcutaneous injection of a colloidal suspension of carrageenan into the plantar face of the rat hind foot, according to a tehnique based on the method of WINTER, RISLEY and NUSS Proc. Soc. Exp. Biol. Med. 111, 554 (1962) and WINEGAR et al. J. Pharmacol. Exp. Ther 166, 96 (1969).

Male WISTAR SPF rats weighing 250±10 g are randomized in batches of 10 and receive the test substances orally 1 hour after the injection of 0.15 cm³ of a 1% suspension of carageenan into the left hind foot. The inflammation is measured 5 hours later by weighting the feet, and the percentage inflammation and anti-inflammatory activity (AIA) values are calculated.

$$\% \text{ Inflammation} = \frac{\text{weight of the inflamed foot} - \text{weight of the control foot}}{\text{weight of the control foot}} \times 100$$

$$\% \text{ AIA} = \frac{\text{mean inflammation of the control batch} - \text{mean inflammation of the treated batch}}{\text{mean inflammation of the control batch}} \times 100$$

| PRODUCT | DOSE | AAI |
|---|---|---|
| 1-[2-(4-phenyl-1-piperazinyl)-ethyl]-1H-oxazolo[5,4-b] pyridin-2-one | 15 mg/kg | 0% |
|  | 150 mg/kg | 12% |
|  | 250 mg/kg | 2% |
| 1-{2-[4-(3-trifluoromethylphenyl)-1-piperazinyl] ethyl}-1H-oxazolo-[5,4-b]pyridin-2-one | 75 mg/kg | 0% |
|  | 200 mg/kg | 0% |
| 1-(2-morpholinoethyl)-1H-oxazolo-[5,4-b]pyridin-2-one | 100 mg/kg | 0% |
|  | 200 mg/kg | 8% |
| Glafenine | 50 mg/kg | 24% |
|  | 150 mg/kg | 28% |
| Aspirin | 150 mg/kg | 12% |

As may be observed, the anti-inflammatory activity of the compounds of the invention is very much lower than that of the reference compounds, including glafenine.

C. STUDY OF GASTRIC TOLERANCE

The gastric tolerability of these compounds was studied by testing for gastric irritation in rats according to a method based on that of LAMBLING (LAMBLING et al. Arch. Mal. Appareil digestif et nutrition (Digestive system and untrition) (1953), 42 p 430).

The test compound are administered orally to male WISTAR SPF rats randomized in batches of 5 and subjected to a water regimen for the previous 24 hours.

After the animals have been housed in restraint cages for six hours wile being deprived of drinking water, the indices of ulceration (U), of hyperemia (H) and of gastric irritation (i) are determined using the modified scoring of LWOFF (LWOFF J. M. J. Pharmacol. Paris (1971) 2 (1) p 81–83).

$$U \text{ or } H = \frac{\text{sum total of scores (U or H)} \times \text{percentage of stomachs showing lesions}}{\text{number of animals studied}}$$

$$i = 3U + H$$

| PRODUCT | DOSE | INDEX OF GASTRIC IRRITATION |
|---|---|---|
| 1-[2-(4-Phenyl-1-piperazinyl)-ethyl]-1H-oxazolo[5,4-b]-pyridin-2-one | 15 mg/kg | 8 |
|  | 75 mg/kg | 8 |
| 1-{2-[4-(3-Trifluoromethylphenyl)-1-piperazinyl]ethyl}-1H-oxazolo-[5,4-b]pyridin-2-one | 75 mg/kg | 8 |
|  | 250 mg/kg | 8 |
| 1-(2-Morpholinoethyl)-1H-oxazolo-[5,4-b]pyridin-2-one | 100 mg/kg | 0 |
|  | 250 mg/kg | 2 |
| Glafenine | 50 mg/kg | 20 |
|  | 250 mg/kg | 240 |
| Aspirin | 250 mg/kg | 146 |
| Indomethacin | 5 mg/kg | 516 |
|  | 10 mg/kg | 570 |

The compounds of the invention hence exhibit very good gastric tolerability in rats.

EXAMPLE 15: Tablets containing 30 MG OF 1-{2-[4-(3-TRIFLUOROMETHYLPHENYL)-1-PIPERAZINYL]ETHYYL}-1H-OXAZOLO[5,4-b]PYRIDIN-2-ONE Preparation formula for 1000 tablets:

| | |
|---|---|
| 1-{2-[4-(3-Trifluoromethylphenyl)-1-piperazinyl]ethyl}-1H-oxazolo[5,4-b]pyridin-2-one | 30 g |
| Wheat starch | 15 g |
| Corn starch | 15 g |
| Lactose | 65 g |
| Magnesium stearate | 1 g |
| Silica | 1 g |
| Hydroxypropylcellulose | 2 g |

We claim:

1. A compound selected from those of formula (I):

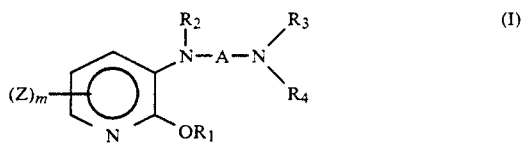

in which:
- $R_1$ and $R_2$, with the oxygen and the nitrogen to which attached, form an —O—CO—N— linkage, corresponding to that of an oxazolo[5,4-b]pyridin-2-one,
- Z represents halogen, linear or branched lower alkyl of 1 to 6 carbon atoms, inclusive linear or branched lower alkoxy of 1 to 6 carbon atoms inclusive, or trifluoromethyl,
- m is 0, 1, 2, or 3,
- A is linear or branched alkyl of 1 to 6 carbon atoms, inclusive
- $R_3$ and $R_4$, which may be identical or different, represent:
  - hydrogen,
  - linear or branched lower alkyl of 1 to 6 carbon atoms, inclusive
  - linear or branched lower alkenyl of 2 to 6 carbon atoms, inclusive
  - optionally substituted aryl,
  - optionally substituted arylalkyl in which the alkyl chain contains 1 to 3 carbon atoms, inclusive
  - mono- or bicyclic cycloalkyl of 3 to 10 carbon atoms, inclusive or alternatively:
- $R_3$ and $R_4$, with the nitrogen atom to which they are linked, constitute a saturated heterocyclic system optionally substituted with one or more:
  - hydroxyl,
  - oxo,
  - linear or branched lower alkyl of 1 to 6 carbon atoms, inclusive
  - optionally substituted aryl,
  - optionally substituted arylalkyl or optionally substituted diarylalkyl in which the alkyl chain contains 1 to 3 carbon atoms, inclusive,
  - —CO—OR$_5$

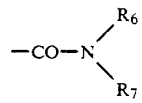

wherein
$R_5$ represents:
- hydrogen,
- linear or branched lower alkyl of 2 to 6 carbon atoms, inclusive
- optionally substituted aryl,
- optionally substituted aralkyl in which the alkyl chain contains 1 to 3 carbon atoms, inclusive $R_6$ and $R_7$, which may be identical or different, have the same meaning as $R_5$,
its isomers, epimers and diastereoisomers,
its addition salts with a pharmaceutically-acceptable acid,
aryl being understood to mean an aromatic, mono- or bicyclic group containing 5 to 12 carbon atoms, inclusive
the term (substituted) associated with the expresions aryl, arylalkyl, and diarylalkyl, meaning that the aryl ring-system can be substituted with one or more linear or branched lower alkyl haviong 1 to 6 carbon atoms, inclusive, linear or branched lower lower alkoxy having 1 to 6 carbon atoms inclusive or hydroxyl, nitro, halogen, or trifluoromethyl.

2. A compound as claimed in claim 1 for which $R_1$ and $R_2$, with the oxygen and the nitrogen to which attached, from an —O—CO—N— link, of formula ($I_A$):

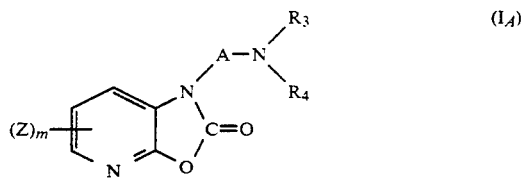

Z, m, A, $R_3$ and $R_4$ having the same meanings as in claim 1, as well as its addition salts with a pharmaceutically-acceptable acid.

3. A compound according to claim 1 in which m=0 and A is a linear alkyl radical having 2 to 6 carbon atoms inclusive.

4. A compound as claimed in claim 1 selected from 1-[2-(4-phenyl-1-piperazinyl)ethyl]-1H-oxazolo[5,4-b]-pyridin-2-one, the formula of which is show below, and its addition salts with a pharmaceutically-acceptable acid.

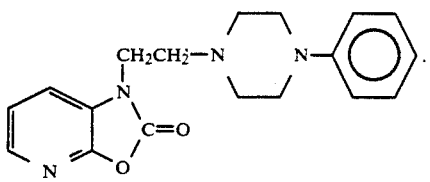

5. A compound as claimed in claim 1 selected from 1-{2-[4-(3-trifluoromethylphenyl)-1-piperazinyl]ethyl}-1H-oxazolo[5,4-b]pyridin-2-one, the formula of which is shown below, and its addition salts with a pharmaceutically-acceptable acid.

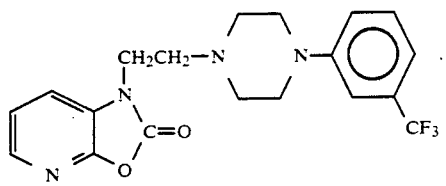

6. A compound as claimed in claim 1 selected from 1-(2-morpholinoethyl)-1H-oxazolo-[5,4-b]pyridin-2-one, the formula of which is shown below, and its addition salts with apharmaceutically-acceptable acid.

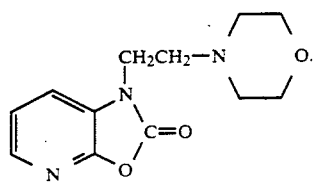

7. A compound as claimed in claim 1 selected from 1-(3-morpholino-1-propyl)-1H-oxazolo[5,4-b]pyridin-2-one, the formula of which is shown below, and its addition salts with a pharmaceutically-acceptable acid.

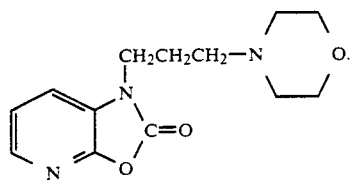

8. A compound as claimed in claim 1 selected from 1-(4-morpholino-1-butyl)-1H-oxazolo[5,4-b]pyridin-2-one, the formula of which is shown below, and its addition salts with a pharmaceutically-acceptable acid.

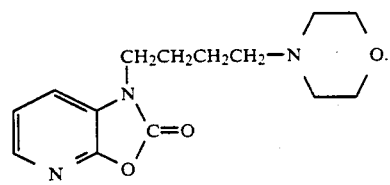

9. A compound as claimed in claim 1 selected from 1-[3-(4-phenyl-1-piperazinyl)-1-propyl]-1H-oxazolo[5,4-b]pyridin-2-one, the formula of which is shown below, and also its addition salts with a pharmaceutically-accetable acid.

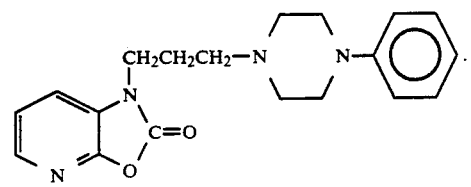

10. A compound as claimed in claim 1 selected from 1-[4-(4-phenyl-1-piperazinyl)-1-butyl]-1H-oxazolo[5,4-b]pyridin-2-one, the formula of which is shown below, and its addition salts with a pharmaceutically-acceptable acid.

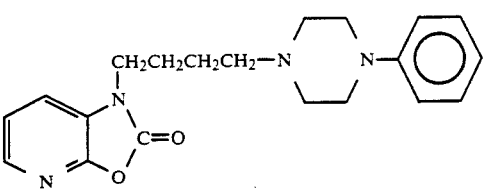

11. A compound as claimed in claim 1 selected from 1-{2-[4-(4-fluorophenyl)-1-piperazinyl]ethyl}-1H-oxazolo[5,4-b]pyridin-2-one, the formula of which is shown below, and its addition salts with a pharmaceutically-acceptable acid.

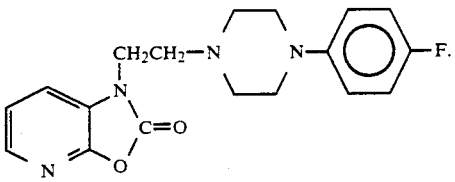

12. A compound as claimed in calim 1 selected from 1-[2-(1-pyrrolidinyl)ethyl]-1H-oxazolo[5,4-b]pyridin-2-one, the formula of which is shown below, and its addition salts with a pharmaceutically-acceptable acid.

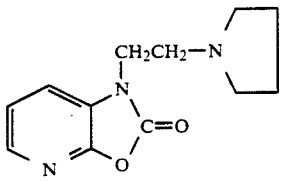

13. A compound as claimed in claim 1 selected from 1-[2-(4-phenyl-1-piperidyl)ethyl]-1H-oxazolo[5,4-b]pyridin-2-one, the formula of which is shown below, and its addition salts with a pharmaceutically-acceptable acid.

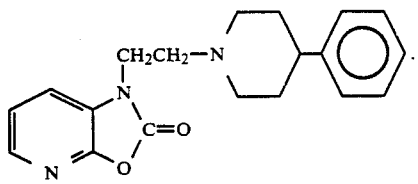

14. A compound as claimed in claim 1 selected from 1-{2-[4-(N,N-diethyl amino carbonyl)-1-piperazing]ethyl}-1H-oxazolo-[5,4-b]pyridin-2-one the formula of which is shown below, and its addition salts with a pharmaceutically-acceptable acid.

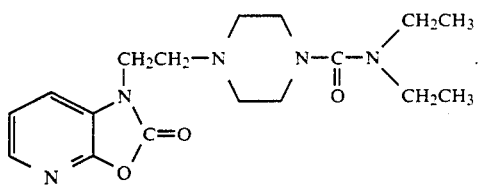

15. A Method for treating a living animal or human afflicted with pain comprising the step of administering to the said living animal or human an amount of a compound of claim 1 which is effective for alleviation of said condition.

16. A pharmaceutical composition, useful for alleviating pain, containing as active principle an effective amount of a compound as claimed in claim 1, in combination which a pharmaceutically accetable excipient or vehicle.

* * * * *

UNITED STATES PATENT AND TRADEMARK OFFICE
CERTIFICATE OF CORRECTION

PATENT NO. : 5,130,311

Page 1 of 4

DATED : Jul. 14, 1992

INVENTOR(S) : Gérald Guillaumet, Christine Flouzat, Michelle Devissaguet, Pierre Renard, Daniel H. Caignard, Gérard Adam It is certified that error appears in the above-identified patent and that said Letters Patent is hereby corrected as shown below:

Column 1, line 9; "[5,4]", second occurrence, should read -- [4,5] --.
Column 1, line 12; "Howver," should read -- However, --.
Column 2, line 2; "carbona toms" should read -- carbon atoms --.
Column 2, line 14; "arylakyl" should read -- arylalkyl --.
Column 2, line 68; "heteroacryl" should read -- heteroaryl --.
Column 3, line 1; "heteroary" should read -- heteroaryl --.
Column 3, line 9/10; "ob-tained" should read -- ob-taining --.
Column 5, approximately line 21; "at temeprature" should read -- at a temperature --.
Column 5, approximately line 35; "acificication" should read -- acidification --.
Column 5, line 53; "compound" should read -- compounds --.
Columm 5, line 54; "unlecerogenic" should read -- ulcerogenic --.
Column 6, line 45; "NH, s 2900" should read -- NH, 2900 --
Column 6, line 46; "CH,s 1775" should read -- CH, 1775 --.
Column 6, line 57; "pyrindin" should read -- pyridin --.
Column 7, line 40; "poihnt:" should read -- point: --.
Column 7, line 41; "2900-3100 cm-1vC=0" should read -- 2900-3100 cm-1 v CH 1760 cm-1 v C = 0 --.
Column 7, line 62; "phydrochloric" should read -- hydrochloric --.
Column 7, line 62; "Ph 1." should read -- pH 1. --.
Column 7, line 63; "ester" should read -- ether --.
Column 7, line 63; "added the" should read -- added and the --.
Column 8, line 12; "portins" should read -- portions --.
Column 8, line 13; "of 1-oxazole" should read -- of 1H-oxazolo--.
Column 8, approximately lines 45,56; delete " $\delta$:7.14 ppm, 1H, doublet of doublet (J=7.3 Hz and J=5.4 Hz) H(6),".
Column 8, line 49; "tripolet" should read -- triplet --.
Column 8, approximately line 68; "ppm, multiplet," should read -- ppm,4H, multiplet, --.
Column 9, line 2; move the "E" at the end of line 2 to the beginning of line 3 before "THYL".
Column 9, line 14; " 'H," should read -- 1H, --.

UNITED STATES PATENT AND TRADEMARK OFFICE
CERTIFICATE OF CORRECTION

PATENT NO. : 5,130,311

Page 2 of 4

DATED : Jul. 14, 1992

INVENTOR(S) : Gérald Guillaumet, Christine Flouzat, Michelle Devissaguet, Pierre Renard, Daniel H. Caignard, Gérard Adam It is certified that error appears in the above-identified patent and that said Letters Patent is hereby corrected as shown below:

Column 9, line 35; " ":3,99" should read -- $\varepsilon$:3,99 --.
Column 9, line 35; "$\delta$3,86" should read -- $\delta$ :3,86 --.
Column 9, line 60; "ETHYL}" should read -- ETHYL] --.
Column 9, line 61; "OXAZOLO≡" should read -- OXAZOLO| --.
Column 10, line 7; "2,54-62" should read -- 2,54-2,62 --.
Column 10, line 56; move the closing parenthesis from the beginning of line 56 to the end of line 55 and insert before the hyphen.
Column 11, line 1; "triple" should read -- triplet --.
Column 11, line 2; "3.26" should read -- 3.62 --.
Column 11, line 18; "2(J=7,9" should read --"2H, triplet (J = 7.9 --.
Column 11, line 45; "3.913" should read -- 3.9 --.
Column 11, line 52; move the closing parenthesis at the beginning of line 52 to the end of line 51 and insert before the hyphen.
Column 11, line 59; "cm-$^1\sqrt{}$ CH," should read --cm-$^1_1$ v CH, --.
Column 11, line 60; "cm-$^1\sqrt{}$ C=O" should read --cm-$^1_1$ v C = O --.
Column 11, line 65; "J = 2.5" should read -- J = 5.2 --.
Column 12, line 9; "cm-$^1\sqrt{}$ CH," should read -- cm-$^1$ v CH,--.
Column 12, approximately line 20; after CH$_2$," second occurrence, insert -- $\delta$:1,56-1,69 ppm, 2H, multiplet CH$_2$ --.
Column 12, line 48; "aqueoius" should read -- aqueous --.
Column 12, line 62; "poential" should read -- potential --.
Column 13, line 13; "wrigthing" should read -- writhing --.
Column 13, line 66; "weighting" should read -- weighing --.
Column 14, line 34; "untrition" should read -- nutrition --.
Column 15, line 40; "inclusive" should read -- inclusive, --. (PA 11-15-91, P. 2, 5th ln.) (Cl. 1)
Column 15, approximately line 45; "inclusive" should read -- inclusive, --.
Column 15, approximately line 47; "inclusive" should read -- inclusive, --.

UNITED STATES PATENT AND TRADEMARK OFFICE
CERTIFICATE OF CORRECTION

PATENT NO. : 5,130,311

Page 3 of 4

DATED : Jul. 14, 1992

INVENTOR(S) : Gérald Guillaumet, Christine Flouzat, Michelle Devissaguet, Pierre Renard, Daniel H. Caignard, Gérard Adam It is certified that error appears in the above-identified patent and that said Letters Patent is hereby corrected as shown below:

Column 15, approximately line 51; "inclusive" should read
-- inclusive, --.
Column 15, approximately line 61; "inclusive" should read
-- inclusive, --.
Column 16, line 10; "2" should read -- 1 --.( Cl. 1)
Column 16, line 11; "inclusive" should read -- inclusive, --.

Column 16, line 14; "inclusive" should read -- inclusive, --.

Column 16, approximately line 22; "inclusive" should read
-- inclusive, --.
Column 16, approximately line 23; "(substituted)" should read
-- "substituted" --.
Column 16, approximately line 26; "haviong" should read
-- having --.
Column 16, approximately line 28; delete "lower". (Cl. 1)
Column 16, approximately line 49, "atoms  inclusive." should read
--atoms, inclusive.--.
Column 18, line 64; "1-piperazing" should read --piperazinyl --

Column 18, line 65/66; move the "e" at the end of line 64 to the beginning of line 65 and insert before "thyl"

UNITED STATES PATENT AND TRADEMARK OFFICE
CERTIFICATE OF CORRECTION

PATENT NO. : 5,130,311

DATED : Jul. 14, 1992

INVENTOR(S) : Gérald Guillaumet, Christine Flouzat, Michelle Devissaguet, Pierre Renard, Daniel H. Caignard, Gérard Adam It is certified that error appears in the above-identified patent and that said Letters Patent is hereby corrected as shown below:

Column 18, line 66; "one the" should read -- one, the --.

Column 20, line 9; "which" should read -- with --.

Column 20, line 9; "pharmaceutically acceptable" should read -- pharmaceutically-acceptable --.

Column 15, line 53; "inclusive" should read -- inclusive, --.

Signed and Sealed this

Twenty-first Day of September, 1993

Attest:

BRUCE LEHMAN

Attesting Officer     Commissioner of Patents and Trademarks